United States Patent [19]

Aruga et al.

[11] Patent Number: 4,957,838

[45] Date of Patent: Sep. 18, 1990

[54] ELECTROPHOTOGRAPHIC PHOTOCONDUCTOR AND TRIPHENYLAMINE COMPOUNDS FOR USE IN THE SAME

[75] Inventors: Tamotsu Aruga, Mishima; Masaomi Sasaki, Susono; Tomoyuki Shimada, Numazu, all of Japan

[73] Assignee: Ricoh Company, Ltd., Tokyo, Japan

[21] Appl. No.: 414,480

[22] Filed: Sep. 29, 1989

[30] Foreign Application Priority Data

Sep. 30, 1988 [JP] Japan .................. 63-247036
Sep. 30, 1988 [JP] Japan .................. 63-247039

[51] Int. Cl.$^5$ .............................................. G03G 5/06
[52] U.S. Cl. .......................................... 430/59; 430/56; 430/58; 564/433
[58] Field of Search ................. 430/59, 57; 564/433

[56] References Cited

FOREIGN PATENT DOCUMENTS 0216853 12/1984 Japan ................................. 564/433
1069069 4/1986 Japan ................................. 564/433
1210363 9/1986 Japan ................................. 564/433

*Primary Examiner*—Paul R. Michl
*Assistant Examiner*—S. C. Crossan
*Attorney, Agent, or Firm*—Oblon, Spivak, McClelland, Maier & Neustadt

[57] ABSTRACT

An electrophotographic photoconductor is disclosed, which comprises an electroconductive support and a photoconductive layer formed thereon comprising as an effective component at least one triphenylamine compound represented by the following formula (I):

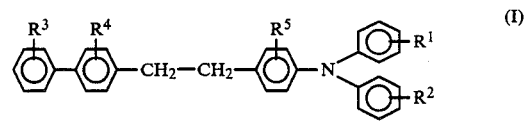

wherein $R^1$, $R^2$, $R^3$, $R^4$ and $R^5$ each represent hydrogen, an alkyl group having 1 to 4 carbon atoms, an alkoxyl group having 1 to 4 carbon atoms, or a halogen, which may be the same or different. Further, novel triphenylamine compounds for use in the electrophotographic photoconductor are disclosed.

20 Claims, 11 Drawing Sheets

ELECTROPHOTOGRAPHIC PHOTOCONDUCTOR AND TRIPHENYLAMINE COMPOUNDS FOR USE IN THE SAME

BACKGROUND OF THE INVENTION

1. Field of the Invention

The present invention relates to an electrophotographic photoconductor and triphenylamine compounds for use as effective components in the photoconductors in particular, to an electrophotographic photoconductor comprising an electroconductive support and a photoconductive layer comprising at least one triphenylamine compound, and novel triphenylamine compounds.

2. Discussion of Background

Conventionally, inorganic materials such as selenium, cadmium sulfide and zinc oxide are used as photoconductive materials of an electrophotographic photoconductor in the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electrical charge of the exposed areas, so that a latent electrostatic image is formed on the photoconductor. The thus formed latent electrostatic image is developed by a developer comprising a coloring agent such as a dye and a pigment, and a binder agent such as a polymeric material, to a visible image.

Fundamental characteristics required for the photoconductor in such an electrophotographic process are: (1) chargeability to an appropriate potential in the dark, (2) minimum dissipation of electrical charge in the dark, and (3) rapid dissipation of electrical charge when exposed to the light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating on a support a dispersion of cadmium sulfide particles and zinc oxide particles in a binder resin. However, they are poor in mechanical properties, such as surface smoothness, hardness, tensile strength and wear resistance. Therefore, they cannot be used in the repeated operation, as they are.

To solve the above-mentioned problems of the inorganic materials, various electrophotographic photoconductors employing organic materials are proposed recently and some are still put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as described in Japanese Patent Publication No. 48-25658; a photoconductor comprising as the main component an organic pigment, as described in Japanese Laid-Open Patent Application No. 47-37543; a photoconductor comprising as the main component an eutectic crystal complex of a dye and a resin, as described in Japanese Laid-Open Patent Application No. 47-10735; a photoconductor prepared by sensitizing a triphenylamine compound with a sensitizer pigment, as described in U.S. Pat. No. 3,180,730; and a photoconductor comprising poly-N-vinylcarbazole and an amine derivative as a charge transporting material, as described in Japanese Laid-Open Patent Application No. 58-1155.

These electrophotographic photoconductors have their own excellent characteristics and considered to be valuable for practical use. With various requirements of the electrophotographic photoconductor in electrophotography taken into consideration, however, there are no electrophotographic photoconductors that can satisfy all the requirements.

SUMMARY OF THE INVENTION

It is therefore a first object of the present invention to provide an electrophotographic photoconductor free from the conventional shortcomings, which can completely satisfy all the requirements in the electrophotographic process, has good durability, and can be easily manufactured at relatively low cost.

A second object of the present invention is to provide a charge transporting material for use in the above-mentioned electrophotographic photoconductor.

A third object of the present invention is to provide novel triphenylamine compounds used as photoconductive materials in the electrophotographic photoconductor.

The first object of the present invention can be achieved by an electrophotographic photoconductor comprising an electroconductive support and a -photoconductive layer formed thereon comprising as an effective component at least one triphenylamine compound represented by the following formula (I) or formula (II):

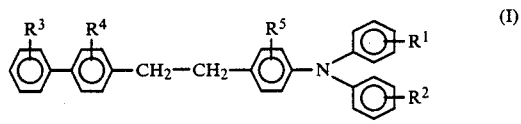

wherein $R^1$, $R^2$, $R^3$, $R^4$ and $R^5$ each represent hydrogen, an alkyl group having 1 to 4 carbon atoms, an alkoxyl group having 1 to 4 carbon atoms, or a halogen, which may be the same or different.

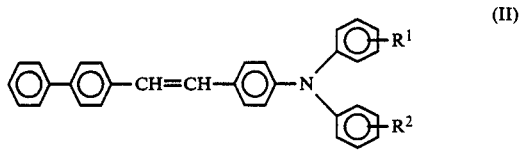

wherein $R^1$ and $R^2$ are the same as those defined in the above formula (I).

The second object of the present invention can be attained by a charge transporting material comprising a triphenylamine compound having the above-mentioned formula (I) or a triphenylamine compound having the above-mentioned formula (II).

The third object of the present invention can be attained by triphenylamine compounds having formula (II) and triphenylamine compounds having formula (III):

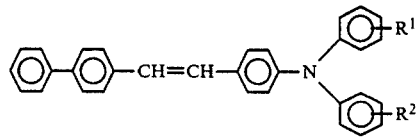

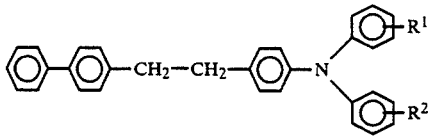

wherein $R^1$ and $R^2$ each represent hydrogen, an alkyl group having 1 to 4 carbon atoms, an alkoxyl group having 1 to 4 carbon atoms, or a halogen, which may be the same or different.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
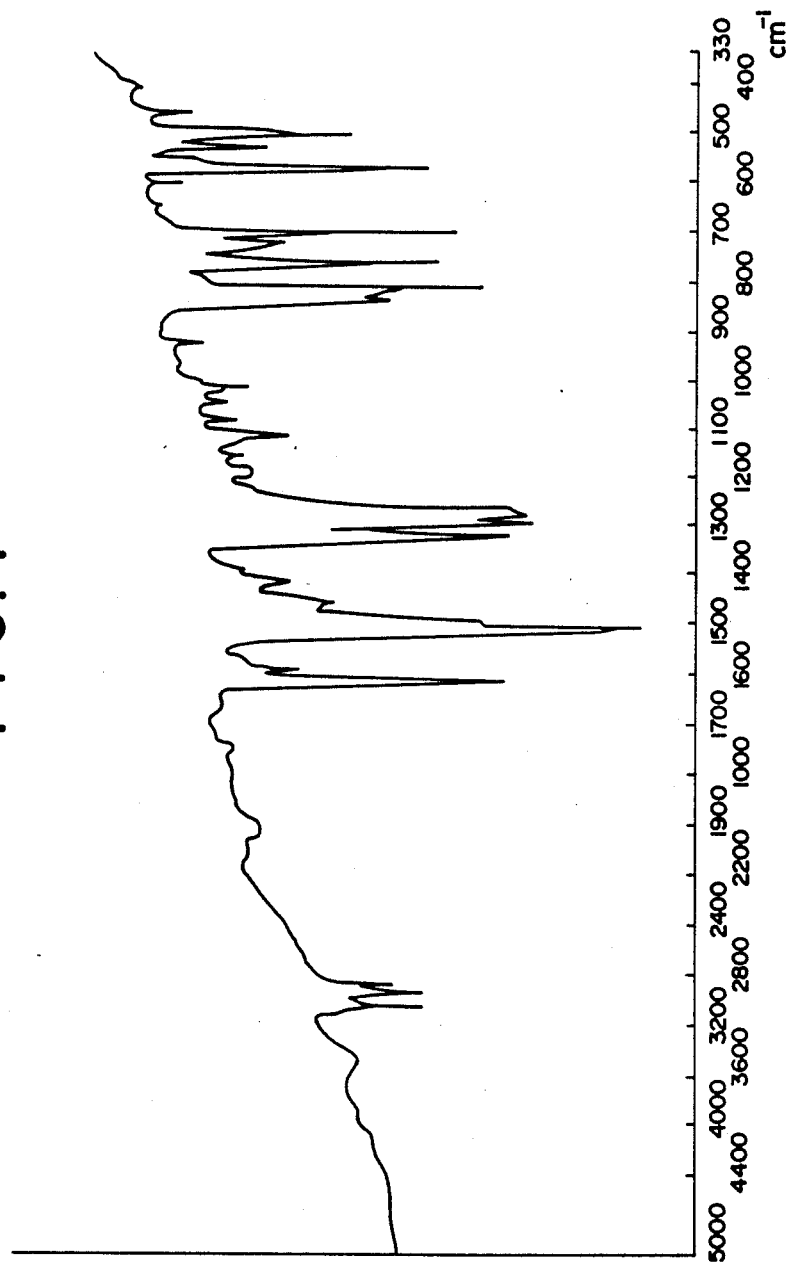
FIGS. 1 through 10 are IR spectra of triphenylamine compounds according to the present invention.
Figure 2:
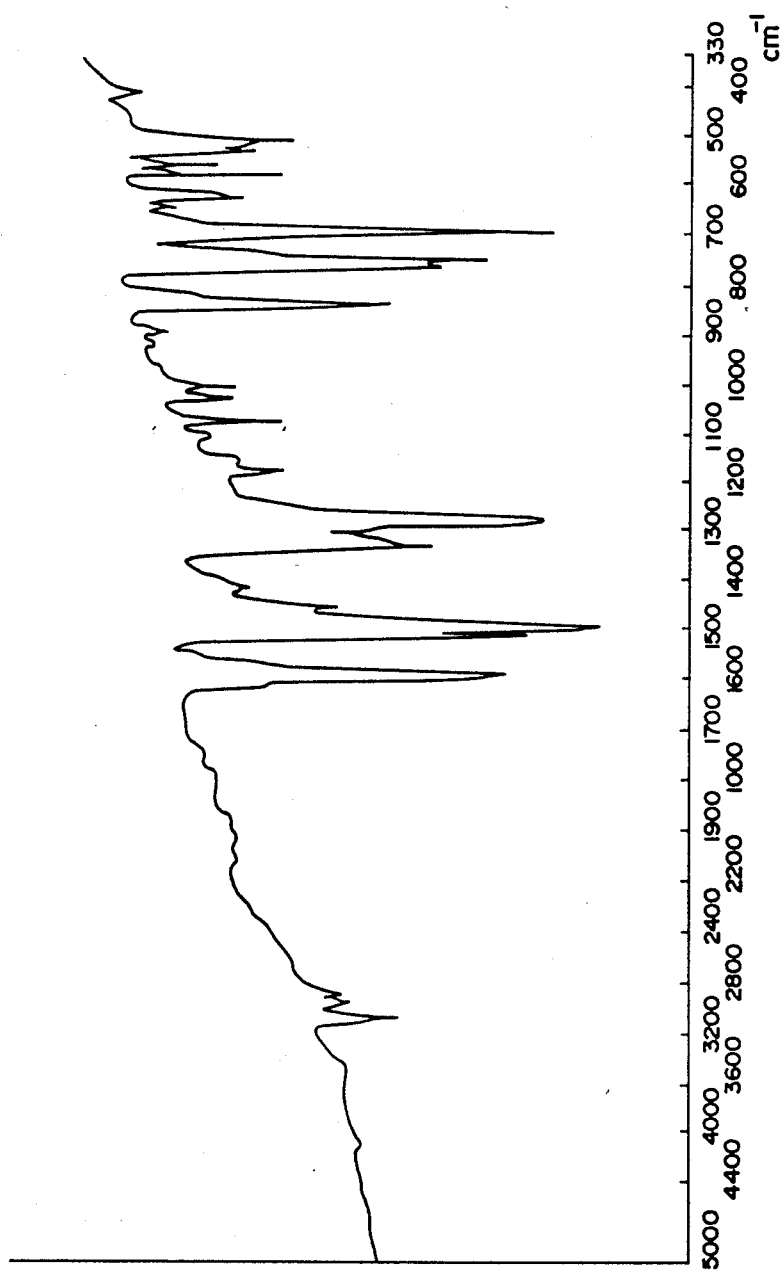
Figure 3:
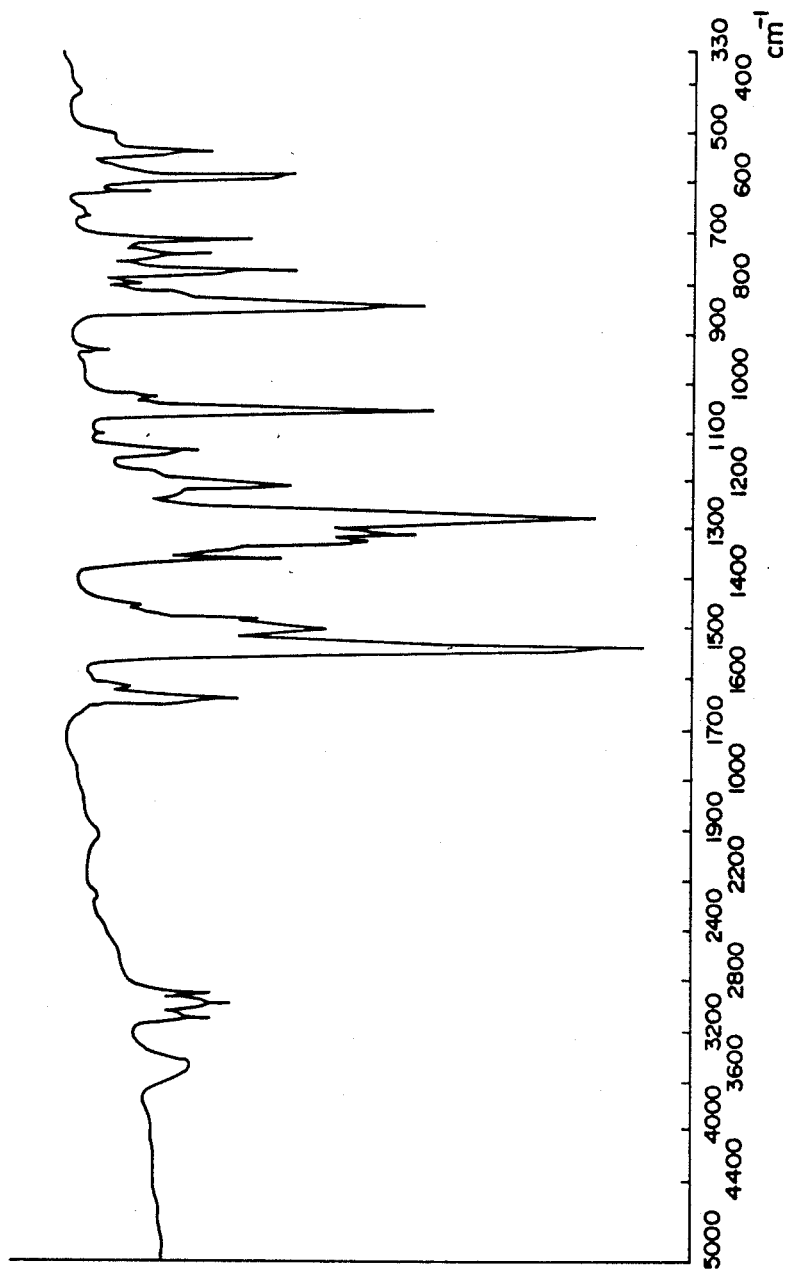
Figure 4:
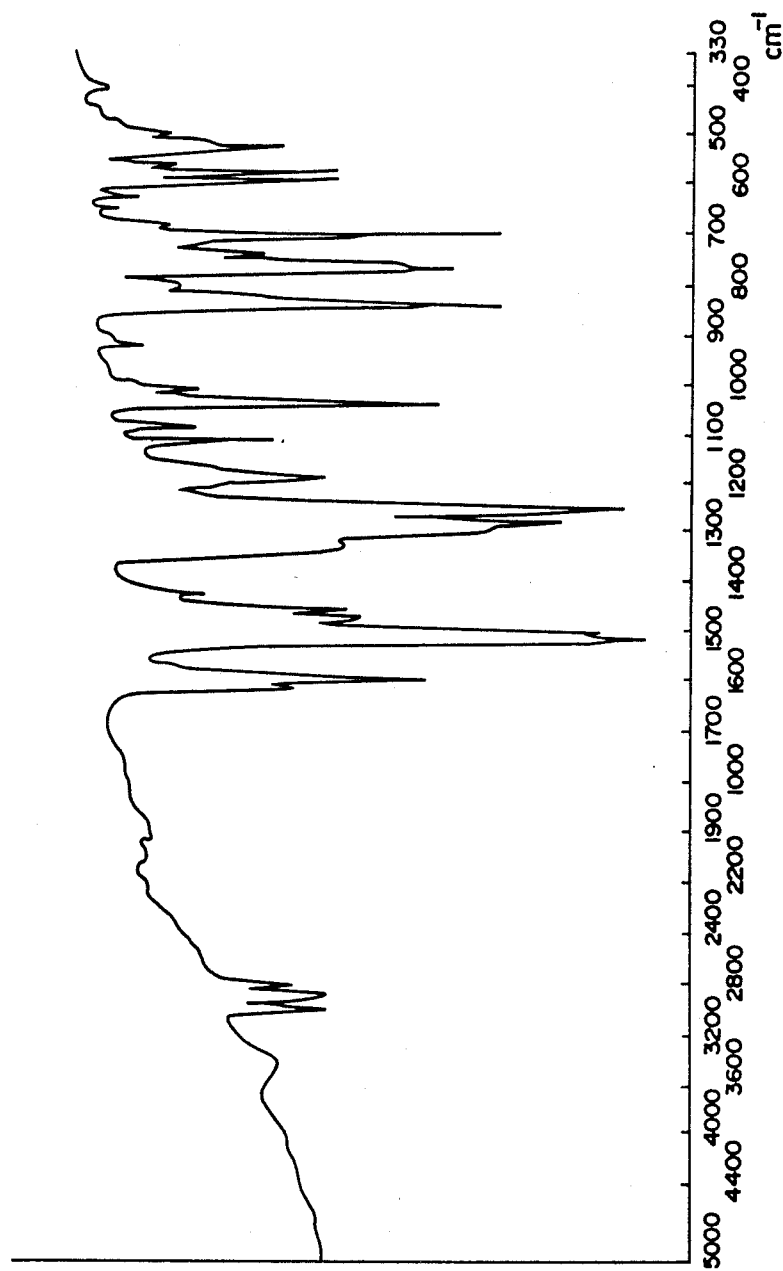
Figure 5:
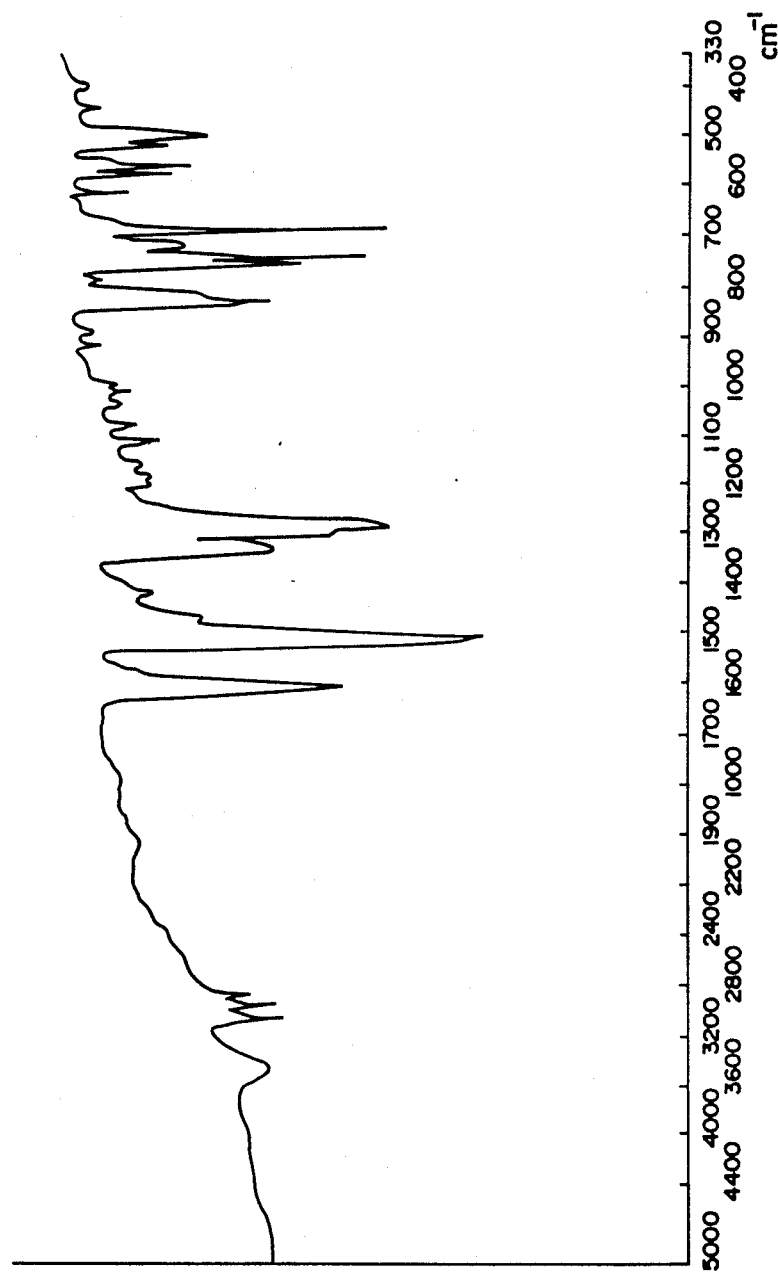

Examples of the triphenylamine compounds of formula (I) or use in the electrophotographic photoconductor according to the present invention are given in the following Table 1.

TABLE 1

| Compound | $R^1$ | $R^2$ | $R^3$ | $R^4$ | $R^5$ |
|---|---|---|---|---|---|
| 1 | H | H | H | H | H |
| 2 | 4-CH₃ | 4-CH₃ | " | " | " |
| 3 | 3-CH₃ | 3-CH₃ | " | " | " |
| 4 | 2-CH₃ | 2-CH₃ | " | " | " |
| 5 | 4-OCH₃ | 4-OCH₃ | " | " | " |
| 6 | 3-OCH₃ | 3-OCH₃ | " | " | " |
| 7 | 2-OCH₃ | 2-OCH₃ | " | " | " |
| 8 | 4-CH₃ | H | " | " | " |
| 9 | 4-OCH₃ | " | " | " | " |
| 10 | 3-CH₃ | " | " | " | " |
| 11 | 3-OCH₃ | " | " | " | " |
| 12 | 4-CH₃ | 4-OCH₃ | " | " | " |
| 13 | 3-Cl | 3-Cl | " | " | " |
| 14 | 2-Cl | 2-Cl | " | " | " |
| 15 | H | H | 4-CH₃ | " | " |
| 16 | 4-CH₃ | 4-CH₃ | " | " | " |
| 17 | 3-CH₃ | 3-CH₃ | " | " | " |
| 18 | 2-CH₃ | 2-CH₃ | " | " | " |
| 19 | 4-OCH₃ | 4-OCH₃ | " | " | " |
| 20 | 3-OCH₃ | 3-OCH₃ | " | " | " |
| 21 | 2-OCH₃ | 2-OCH₃ | " | " | " |
| 22 | 4-CH₃ | H | " | " | " |
| 23 | 4-OCH₃ | H | 4-CH₃ | H | H |
| 24 | 3-CH₃ | " | " | " | " |
| 25 | 3-OCH₃ | " | " | " | " |
| 26 | 4-CH₃ | 4-OCH₃ | " | " | " |
| 27 | 3-Cl | 3-Cl | " | " | " |
| 28 | 2-Cl | 2-Cl | " | " | " |
| 29 | H | H | 4-OCH₃ | " | " |
| 30 | 4-CH₃ | 4-CH₃ | " | " | " |
| 31 | 3-CH₃ | 3-CH₃ | " | " | " |
| 32 | 2-CH₃ | 2-CH₃ | " | " | " |
| 33 | 4-OCH₃ | 4-OCH₃ | " | " | " |
| 34 | 3-OCH₃ | 3-OCH₃ | " | " | " |
| 35 | 2-OCH₃ | 2-OCH₃ | " | " | " |
| 36 | 4-CH₃ | H | " | " | " |
| 37 | 4-OCH₃ | " | " | " | " |
| 38 | 3-CH₃ | " | " | " | " |
| 39 | 4-CH₃ | 4-CH₃ | 3-CH₃ | " | |
| 40 | 4-CH₃ | 4-CH₃ | H | H | 2-CH₃ |

Of the triphenylamine compounds of formula (I), the triphenylamine compounds of the following formula (III) are novel:

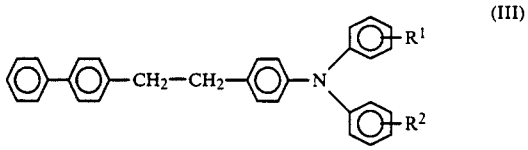

wherein $R^1$ and $R^2$ each represent hydrogen, an alkyl group having 1 to 4 carbon atoms, an alkoxyl group having 1 to 4 carbon atoms, or a halogen, which may be the same or different.

Furthermore, the triphenylamine compounds having the following formula (II) are also novel compounds.

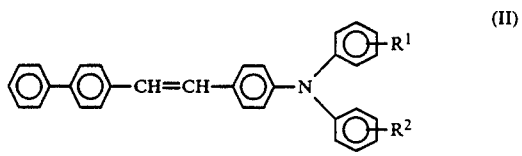

wherein $R^1$ and $R^2$ are the same as those defined in the above formula (III).

The triphenylamine compounds of formula (III) according to the present invention, any of which can be contained in a photoconductive layer of an electrophotographic photoconductor, can be obtained, for example, by reducing the compounds represented by the above formula (II) by catalystic hydrogenation:

In the catalystic hydrogenation, homogeneous and heterogeneous catalysts are generally employed. Examples of a homogeneous catalyst are complex compounds of metallic elements belonging to the group VIII in the periodic table of elements, such as rhodium, ruthenium, iridium and cobalt. Examples of a heterogeneous catalyst are platinum compounds, Raney nickel catalysts, and catalysts so constructed that platinum, palladium, rhodium or ruthenium is supported by activated carbon, alumina or barium sulfate. In the present invention, the above-mentioned heterogeneous catalysts are preferable from the viewpoint of the convenience of after-treatment.

When a heterogeneous catalyst is employed in the above reaction, the reduction is initiated by vigorously stirring the compound, with the atmosphere replaced with a hydrogen gas of 1 atm. in a sealed system. In this case, the hydrogen gas is supplied to the system through a pressure reducing valve, as absorbed in the course of the reaction. When the stoichiometric amount of the hydrogen gas is absorbed by the compound, the absorption is terminated, and the reduction is completed. The reduction may be carried out at room temperature. In the case where the hydrogen gas is not readily absorbed by the compound, the system may be heated in the course of the reduction. Examples of a solvent for the reduction are methanol, ethanol, propanol, tetrahydrofuran, dioxane and acetic acid.

The triphenylamine compounds of formula (II) can be easily obtained by allowing a phosphonium salt having the following formula (IV) to react with an aldehyde compound having the following formula (V) in an organic solvent in the presence of a basic material.

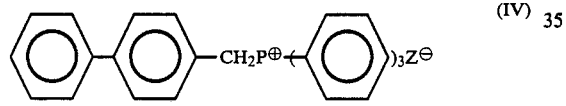
(IV)

wherein $Z^{\ominus}$ represents a halogen ion.

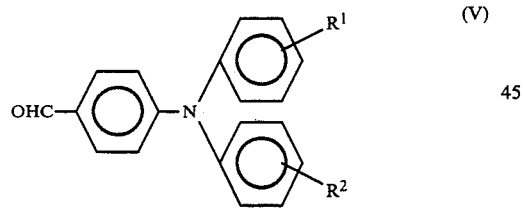
(V)

wherein $R^1$ and $R^2$ are the same as previously defined.

Examples of the basic material for use in the above-mentioned reaction are sodium hydroxide, potassium hydroxide, sodium amide, an alcoholate such as sodium methylate, potassium methylate and potassium-t-butoxide, and n-butyl lithium.

Examples of the reaction solvent for use in the above reaction are tetrahydrofuran, dioxane, bis(2-methoxyethyl) ether, 1,2-dimethoxyethane, methanol, ethanol, toluene, xylene, dimethyl sulfoxide, N,N-dimethylformamide, N-methylpyrrolidone and 1,3-dimethyl-2-imidazolydinone.

In the reaction of the phosphonium salt with the aldehyde compound, the reaction temperature can be set in a relatively wide range, depending on (1) the stability of the employed solvent to the basic material; (2) the reactivity of the phosphonium salt such as 4-phenylbenzyl triphenylphosphonium bromide and the aldehyde compound; and (3) the reactivity of the above-mentioned compounds in the presence of the basic material. For example, it is preferable that the reaction temperature be set in the range of 5° to 50° C., more preferably in the range of 5° C. to room temperature when a polar solvent is employed. When it is desired to shorten the reaction time, or when the activity of the folmaldehyde compound employed is low, the reaction temperature may be further elevated.

Examples of the novel triphenylamine compounds of formulas (II) and (III) are as follows:

[Triphenylamine Compounds of Formula (II)]

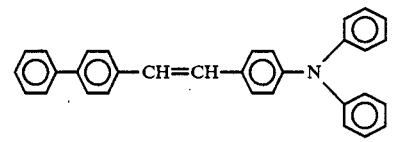

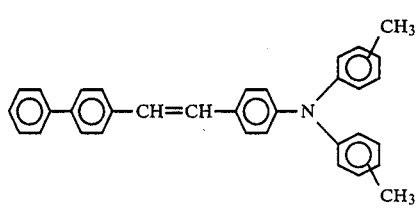

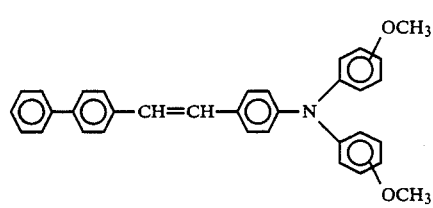

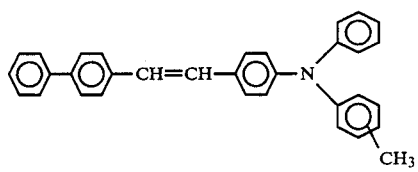

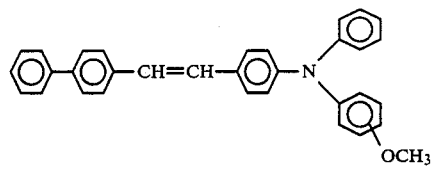

[Triphenylamine Compounds of Formula (III)]

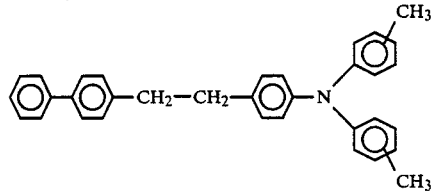

(Triphenylamine comounds Nos. 2, 3 and 4 in Table 1)

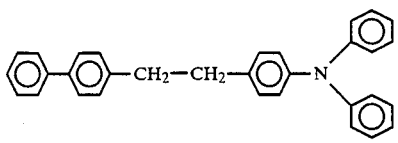

-continued (Triphenylamine compound No. 1 in Table 1)

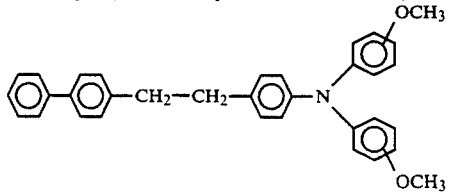

(Triphenylamine compounds Nos. 5, 6 and 7 in Table 1)

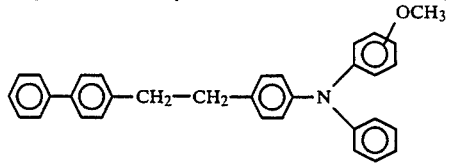

(Triphenylamine compounds Nos. 9 and 11 in Table 1)

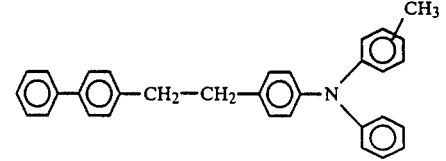

(Triphenylamine compounds Nos. 8 and 10 in Table 1)

The triphenylamine compounds of formula (I) and triphenylamine compounds of formula (II) are effective as photoconductive materials in the electrophotographic photoconductor and optically or chemically sensitized with a sensitizer such as a dye or a Lewis acid. In particular, the triphenylamine compounds of formula (I) are effective as photoconductive materials. In addition, the triphenylamine compounds effectively function as a charge transporting material in a function-separating type electrophotographic photoconductor where an organic or inorganic pigment serves as a charge generating material.

In the electrophotographic photoconductor according to the present invention, at least one triphenylamine compound of formula (I) or a triphenylamine compound of formula (II) is contained in a photoconductive layer 2, 2a, 2b or 2c in FIGS. 11 to 14. The triphenylamine compounds can be employed in different ways, for example, as shown in FIGS. 11 to 14.

Figure 11:
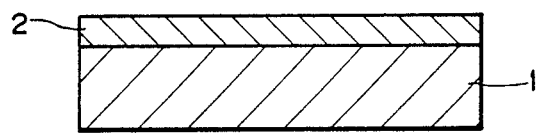
FIG. 11 is a schematic cross-sectional view of an example of an electrophotographic photoconductor according to the present invention.

In the photoconductor as shown in FIG. 11, there is formed on an electroconductive support 1 a photoconductive layer 2 comprising any of the triphenylamine compounds, a sensitizing dye and a binder agent (binder resin). In this photoconductor, the triphenylamine compound functions as a photoconductive material, through which charge carriers which are necessary for the light decay of the photoconductor are generated and transported. However, the triphenylamine compound itself scarcely absorbs light in the visible light range and, therefore, it is necessary to add a sensitizing dye which absorbs light in the visible light range in order to form latent electrostatic images by use of visible light.

Figure 12:
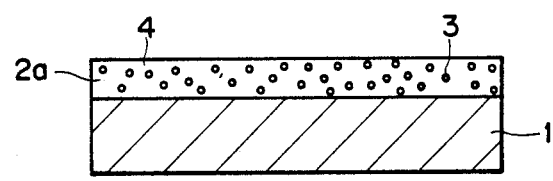
FIG. 12 is a schematic cross-sectional view of another second example of an electrophotographic photoconductor according to the present invention.

In the photoconductor as shown in FIG. 12, a photoconductive layer 2a is formed on an electroconductive support 1, which photoconductive layer 2a comprises a charge generating material 3 dispersed in a charge transporting medium 4 comprising the triphenylamine compound and a binder agent. In this embodiment, the triphenylamine compound and the binder agent (or the mixture of a binder agent and a plasticizer) constitute the charge transporting medium 4 in combination. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the triphenylamine compounds not overlap in the visible light range. This is because it is necessary that light pass through the surface of the charge generating material 3 in order that the charge generating material 3 produce charge carriers efficiently. Since the triphenylamine compounds having the above-described formula (I) do not substantially absorb light in the visible range, they can work effectively as charge transporting materials in combination with the charge generating material 3 which absorbs the light in the visible region and generates charge carriers.

Figure 13:
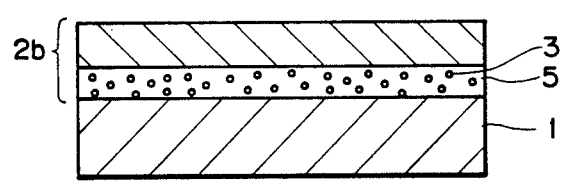
FIG. 13 is a schematic cross-sectional view of a further third example of an electrophotographic photoconductor according to the present invention.

In the photoconductor as shown in FIG. 13, there is formed on the electroconductive support 1 a two-layered photoconductive layer 2b comprising a charge generation layer 5 consisting essentially of the charge generating material 3, and a charge transport layer 6 containing the triphenylamine compound.

In this photoconductor, light which has passed through the charge transport layer 6 reaches the charge generation layer 5, and charge carriers are generated within the charge generation layer 5. The charge carriers which are necessary for the light decay for latent electrostatic image formation are generated by the charge generating material 3, accepted and transported by the charge transport layer 6. In the charge transport layer 6, the triphenylamine compound mainly works for transporting the charge carriers. The generation and transportation of the charge carriers are performed by the same mechanism as that in the photoconductor shown in FIG. 12.

When an electrophotographic photoconductor according to the present invention as shown in FIG. 11 is prepared, at least one triphenylamine compound is dissolved in a binder resin solution, and a sensitizing dye is then added to the above-prepared mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the triphenylamine compound contained in the photoconductive layer 2 be in the range of 30 to 70 wt. %, more preferably about 50 wt. %.

It is preferable that the amount of the sensitizing dye contained in the photoconductive layer 2 be in the range of 0.1 to 5 wt. %, more preferably in the range of 0.5 to 3 wt. %.

Specific examples of the sensitizing dye for use in the present invention are: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; pyrylium dyes such as 2,6-diphenyl-4-(N,N- dimethylaminophenyl)thiapyrylium perchlorate and benzopyrylium salts (Japanese Patent Publication No. 48-25658); and 2,4,7-trinitro-9-fluorenone and 2,4-dinitro-9-fluorenone. These sensitizing dyes may be used alone or in combination.

The electrophotographic photoconductor shown in FIG. 12 can be obtained by dispersing finely-divided particles of the charge generating material 3 in a solution in which at least one triphenylamine compound for use in the present invention and the binder agent are dissolved, coating the above-prepared dispersion on the electroconductive support and then drying the same to form the photoconductive layer 2a.

It is preferable that the thickness of the photoconductive layer 2a be in the range of 3 to 50 $\mu$m, more preferably in the range of 5 to 20 $\mu$m. It is preferable that the amount of the triphenylamine compound contained in the photoconductive layer 2a be in the range of 10 to 95 wt. %, more preferably in the range of 30 to 90 wt. %.

It is preferable that the amount of the charge generating material 3 contained in the photoconductive layer 2a be in the range of 0.1 to 50 wt. %, more preferably in the range of 1 to 20 wt. %.

Specific examples of the charge generating material 3 for use in the present invention are as follows: inorganic pigments such as selenium, selenium - tellurium, cadmium sulfide, cadmium sulfide - selenium and $\alpha$-silicone; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application No. 53-95033), an azo pigment having a distyryl benzene skeleton (Japanese Laid-Open Patent Application No. 53-133445), an azo pigment having a triphenylamine skeleton (Japanese Laid-Open Patent Application No. 53-132347), an azo pigment having a dibenzothiophene skeleton (Japanese Laid-Open Patent Application 54-21728), an azo pigment having an oxadiazole skeleton (Japanese Laid-Open Patent Application No. 54-12742), an azo pigment having a fluorenone skeleton (Japanese Laid-Open Patent Application No. 54-22834), an azo pigment having a bisstilbene skeleton (Japanese Laid-Open Patent Application No. 54-17733), an azo pigment having a distyryl oxadiazole skeleton (Japanese Laid-Open Patent Application No. 54-2129), and an azo pigment having a distyryl carbazole skeleton (Japanese Laid-Open Patent Application No. 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials may be used alone or in combination.

The electrophotographic photoconductor shown in FIG. 13 can be obtained as follows:

The charge generating material is vacuum-deposited on the electroconductive support 1, or a dispersion in which finely-divided particles of the charge generating material 3 is dispersed in an appropriate solvent together with the binder agent when necessary is coated on the electroconductive support 1 and dried, so that the charge generation layer 5 is formed. When necessary, the charge generation layer 5 is subjected to buffing to adjust the thickness thereof. On the thus formed charge generation layer 5, a coating solution in which at least one triphenylamine compound and the binder agent are dissolved is coated and dried, so that the charge transport layer 6 is formed on the charge generation layer 5. In the charge generation layer 5, the same charge generating materials as employed in the above-mentioned photoconductive layer 2a can be used.

The thickness of the charge generation layer 5 is 5 $\mu$m or less, more preferably 2 $\mu$m or less. It is preferable that the thickness of the charge transport layer 6 be in the range of 3 to 50 $\mu$m, more preferably in the range of 5 to 20 $\mu$m. When the charge generation layer 5 is obtained by coating the dispersion in which finely-divided particles of the charge generating material 3 is dispersed in an appropriate solvent together with the binder agent, it is preferable that the amount of finely-divided particles of the charge generating material 3 contained in the charge generation layer 5 be in the range of 10 to 95 wt. %, more preferably in the range of about 50 to 90 wt. %. It is preferable that the amount of the triphenylamine compound contained in the charge transport layer 6 be in the range of 10 to 95 wt. %, more preferably in the range of 30 to 90 wt. %.

Figure 14:
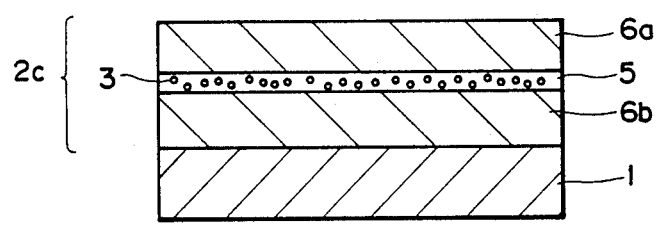
FIG. 14 is a schematic cross-sectional view of still another example of the present invention.

An electrophotographic photoconductor with a structure as shown in FIG. 14 may also be employed in the present invention, which can be obtained by forming a charge transport layer 6a, a charge generation layer 5, and a charge transport layer 6b successively in that order on an electroconductive support 1, in which one of the charge transport layer 6a or the charge transport layer 6b comprises at least one triphenylamine compound and the other charge transport layer comprises a Lewis acid type charge transporting material, for example, fluorenone compounds such as trichlorofluorenone, and quinone derivatives.

Specific examples of the electroconductive support for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive force can be employed. Some plasticizers may be added to the above-mentioned binder agent, when necessary. Examples of the plasticizer for use in the present invention are halogenated paraffin, polyvinyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 $\mu$m or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed with a developer to a visible image, and when necessary, the developed image can be transferred to a sheet of paper. The electrophotographic photoconductors according to the present invention have the advantages over conventional photoconductors that the photosensitivity is high and the flexibility is improved.

Other features of this invention will become apparent in the course of the following description of exemplary embodiments, which are given for illustration of the invention and are not intended to be limiting thereof.

SYNTHESIS EXAMPLE 1

[Synthesis of Triphenylamine Compound No. 2 in Table 1]

A mixture of 5.1 g of 4-phenylbenzyl triphenylphosphonium bromide and 3.0 g of 4-[N,N-bis(p-tolyl)amino]benzaldehyde was added to 60 ml of tetrahydrofuran. A 15% hexane solution containing 6.4 g of n-butyl lithium was added dropwise to the above mixture, with stirring in a stream of nitrogen, over a period of about 80 minutes. In the course of addition of the 15% hexane solution of n-butyl lithium, iced water was added to the reaction mixture to keep its temperature at 10° to 14° C. After the reaction mixture was stirred at room temperature for about 1 hour, the reaction mixture was poured into 100 ml of water. The mixture was extracted with toluene and the solvent was removed therefrom. The reaction product was isolated from the reaction mixture by column chromatography using silica gel (Trademark "Wakogel C-200" made by Wako Pure Chemical Industries, Ltd.) as a carrier and a mixed solvent of n-hexane and toluene with a mixing ratio of 1:1 as a developing solvent. The product was refluxed in 150 ml of cyclohexane in the presence of a small quantity of iodine to convert the product into a trans-product. The solvent was removed from the reaction mixture and then the product was recrystallized from a mixed solvent of toluene and n-hexane, whereby 4-[4-N,N-bis(p-tolyl)amino]styrylbiphenyl was obtained in a 51% yield.

1.45 g of the above prepared 4-[4-N,N-bis(p-tolyl)amino]styrylbiphenyl was dissolved in 50 ml of a 5% tetrahydrofuran solution containing 0.15 g of palladium carbon. The thus obtained mixture was vigorously stirred at room temperature to initiate the reaction, with a hydrogen gas introduced therein. When the mixture absorbed 80 ml of the hydrogen gas, the reaction was terminated. The reaction mixture was subjected to filtration, concentration and then column chromatography using silica gel as a carrier and a mixed solvent of toluene and n-hexane with a mixing ratio of 2:1 as a developing solvent, so that a white powder was obtained. The thus obtained white powder was recrystallized from a mixed solvent of ethanol and acetic acid ethyl, whereby 1.3 g of 1-[4-N,N-bis(p-tolyl)aminophenyl]-2-(4-biphenyl)ethane (triphenylamine compound No. 2 in Table 1) was obtained in the form of colorless needles in a 90% yield. The melting point was 135.5° to 136.0° C.

The results of the elemental analysis of the thus obtained product were as follows:

|  | % C | % H | % N |
|---|---|---|---|
| Calculated | 90.02 | 6.89 | 3.09 |
| Found | 89.75 | 6.69 | 2.90 |

The above calculation was based on the formula for 1-[4-N,N-bis(p-tolyl)aminophenyl]-2-(4-biphenyl)ethane of $C_{34}H_{31}N$.

FIG. 1 shows an infrared spectrum of the above obtained 1-[4-N,N-bis(p-tolyl)aminophenyl]-2-(4-biphenyl)ethane, taken by use of a KBr tablet.

SYNTHESIS EXAMPLES 2 TO 5

The procedure for Synthesis Example 1 was repeated except that 4-[4-N,N-bis(p-tolyl)amino]styrylbipheyl employed in Synthesis Example 1 was replaced by the following compounds shown in Table 2, whereby triphenylamine compounds according to the present invention were respectively obtained.

The melting points and the results of the elemental analysis of the thus obtained triphenylamine compounds according to the present invention are also shown in Table 2. FIGS. 2 through 5 show the infrared spectra of the thus obtained triphenylamine compounds, taken by use of a KBr tablet.

TABLE 2

| Synthesis Example NO. | Compounds Employed in Reaction | Obtained Products | | Elemental Analysis Found (Calculated) | | |
|---|---|---|---|---|---|---|
| | Formula | Formula | Melting Point (°C.) | (%)C | (%)H | (%)N |
| 1 | [structure with CH=CH, biphenyl, N(tolyl)₂] | [structure with CH₂—CH₂, biphenyl, N(tolyl)₂] (Triphenylamine Compound No. 2 in Table 1) | 135.5–136.0 | 89.75 (90.02) | 6.69 (6.89) | 2.90 (3.09) |
| 2 | [structure with CH=CH, biphenyl, NPh₂] | [structure with CH₂—CH₂, biphenyl, NPh₂] (Triphenylamine Compound No. 1 in Table 1) | 117.5–118.5 | 90.16 (90.31) | 6.31 (6.39) | 3.16 (3.29) |
| 3 | [structure with CH=CH, biphenyl, N(p-anisyl)₂] | [structure with CH₂—CH₂, biphenyl, N(p-anisyl)₂] (Triphenylamine Compound No. 5 in Table 1) | 102.5–103.0 | 84.30 (84.09) | 6.35 (6.43) | 2.64 (2.88) |
| 4 | [structure with CH=CH, biphenyl, N(p-anisyl)(Ph)] | [structure with CH₂—CH₂, biphenyl, N(p-anisyl)(Ph)] (Triphenylamine Compound No. 9 in Table 1) | 91.0–92.0 | 87.09 (87.00) | 6.29 (6.42) | 2.81 (3.07) |

TABLE 2-continued

| Synthesis Example NO. | Compounds Employed in Reaction | Obtained Products | | Elemental Analysis Found (Calculated) | | |
| --- | --- | --- | --- | --- | --- | --- |
| | | Formula | Melting Point (°C.) | (%)C | (%)H | (%)N |
| 5 | [structure with CH=CH linkage, biphenyl and N(phenyl)(tolyl) groups] | [structure with CH₂—CH₂ linkage, biphenyl and N(phenyl)(tolyl) groups] (Triphenylamine Compound No. 8 in Table 1) | 120.5–121.0 | 90.15 (90.16) | 6.61 (6.65) | 2.95 (3.19) |

SYNTHESIS EXAMPLE 6

A mixture of 5.1 g of 4-phenylbenzyl triphenylphosphonium bromide and 3.0 g of 4-[N,N-bis(p-tolyl)amino]benzaldehyde was added to 60 ml of tetrahydrofuran. A 15% hexane solution containing 6.4 g of n-butyl lithium was added dropwise to the above mixture, with stirring in a stream of nitrogen, over a period of about 80 minutes. In the course of addition of the 15% hexane solution of n-butyl lithium, iced water was added to the reaction mixture to keep its temperature at 10° to 14° C. After the reaction mixture was stirred at room temperature for about 1 hour, the reaction mixture was poured into 100 ml of water. The mixture was extracted with toluene and the solvent was removed therefrom. The reaction product was isolated from the reaction mixture by column chromatography using silica gel (Trademark "Wakogel C-200" made by Wako Pure Chemical Industries, Ltd.) as a carrier and a mixed solvent of n-hexane and toluene with a mixing ratio of 1:1 as a developing solvent. The product wa refluxed in 150 ml of cyclohexane in the presence of a small quantity of iodine to convert the product into a trans-product. The solvent was removed from the reaction mixture and then the product was recrystallized from a mixed solvent of toluene and n-hexane, whereby 2.3 g of 4-[4-N,N-bis(p-tolyl)amino]-styrylbiphenyl was obtained in the form of light yellow needles in a 51% yield.

The melting point and the results of the elemental analysis of the thus obtained product are shown in Table 3.

Figure 6:
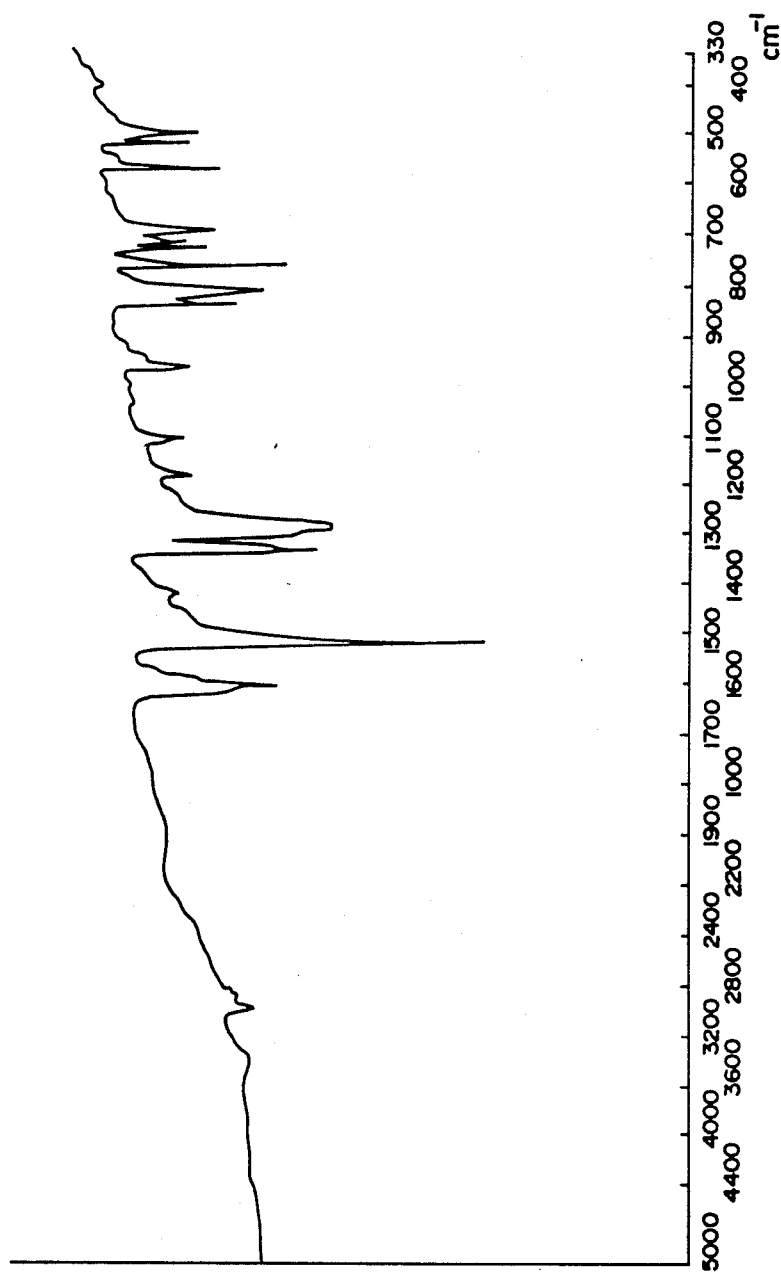
Figure 7:
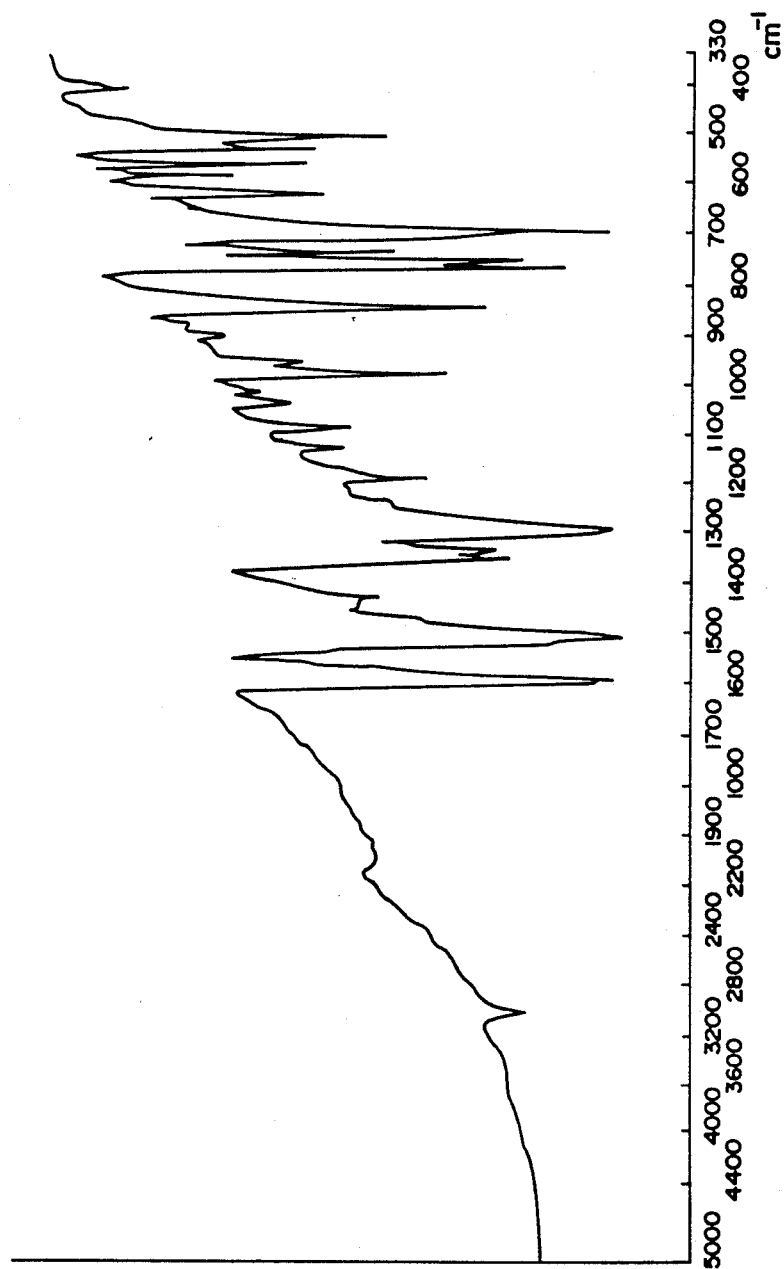
Figure 8:
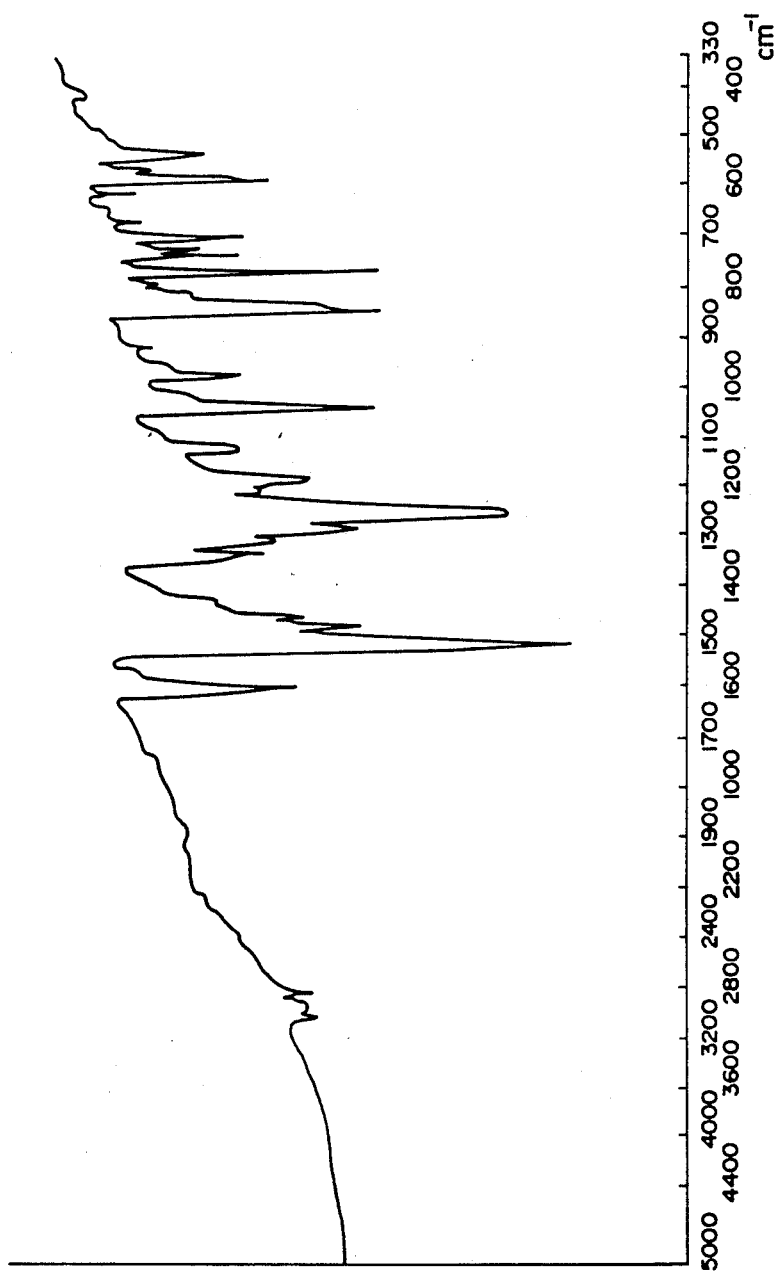
Figure 9:
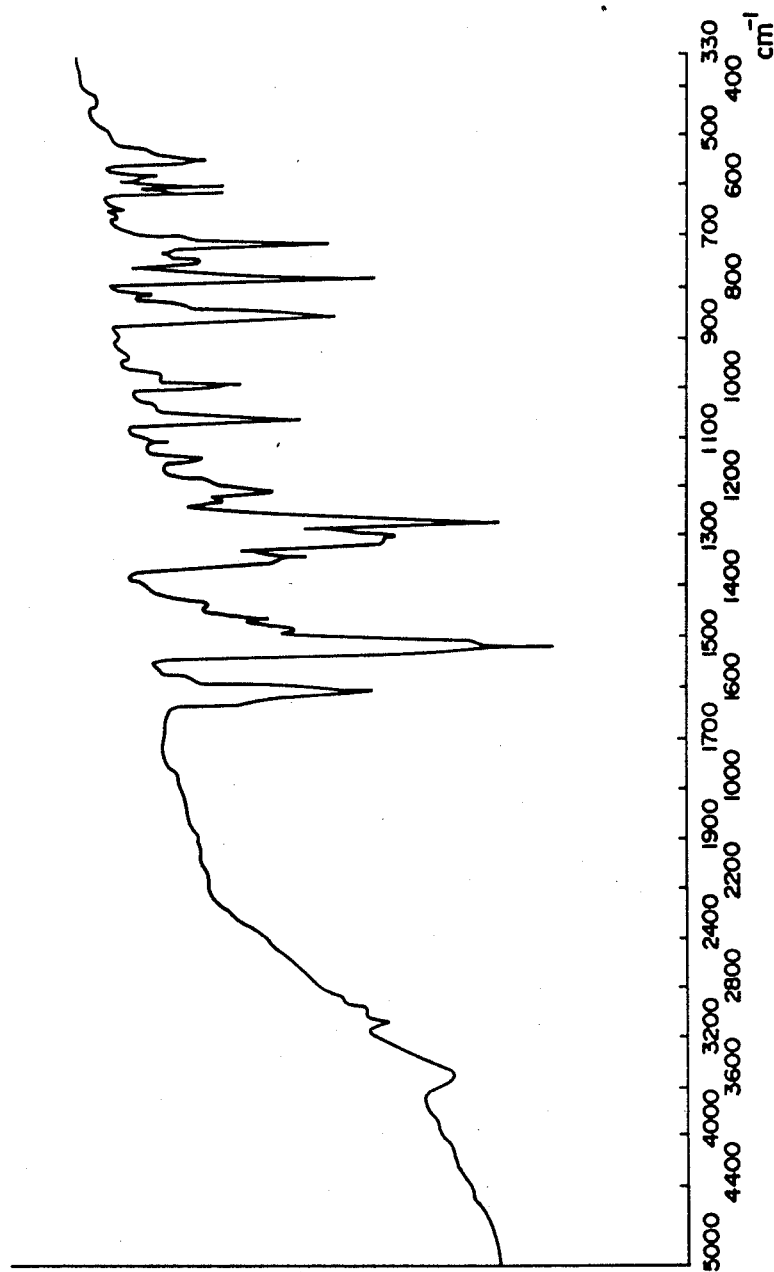
Figure 10:
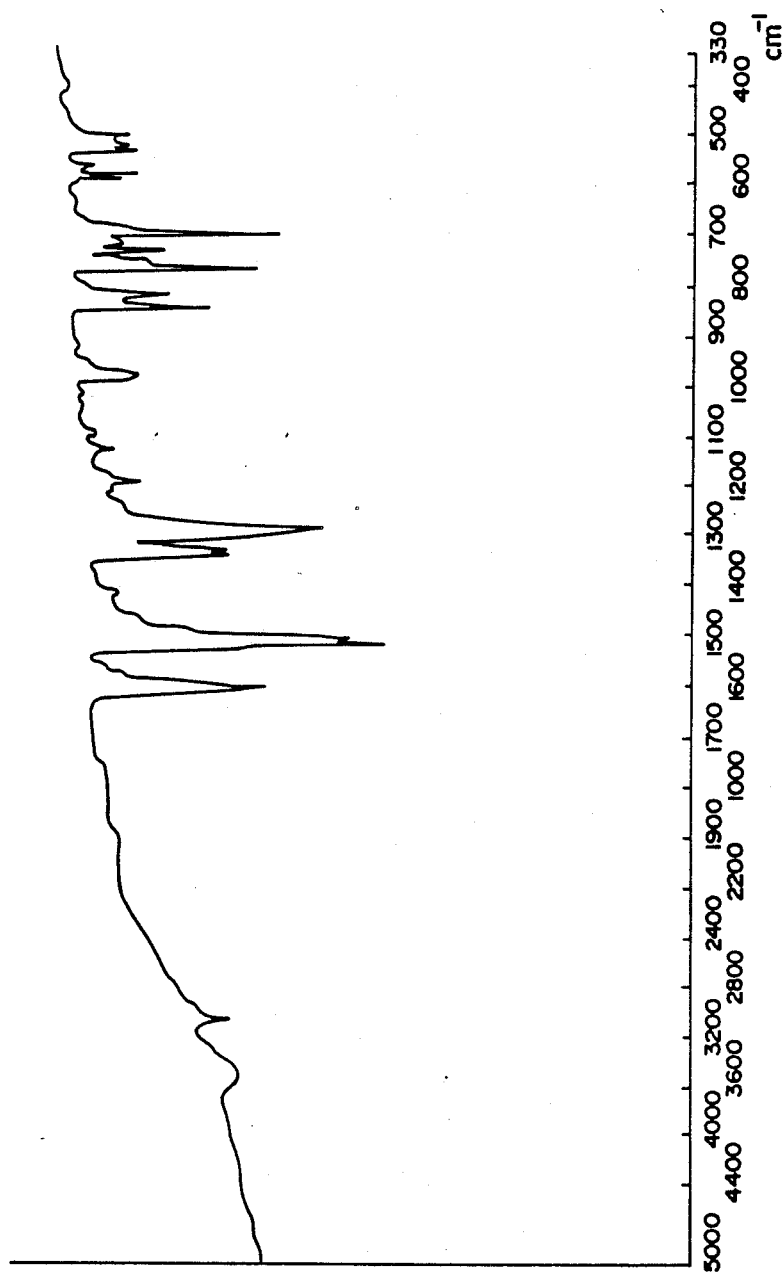

FIG. 6 shows an infrared spectrum of the above obtained 4-[4-N,N-bis(p-tolyl)amino]styrylbiphenyl, taken by use of a KBr tablet, which indicates an absorption at 970 $cm^{-1}$ characteristic of deformation vibration of trans-olefin.

SYNTHESIS EXAMPLES 7 TO 10

The procedure for Synthesis Example 6 was repeated except that 4-[4-N,N-bis(p-tolyl)amino]benzaldehyde employed in Synthesis Example 6 was replaced by the following aldehyde compounds shown in Table 3, whereby triphenylamine compounds according to the present invention were respectively obtained.

The melting points and the results of the elemental analysis of the thus obtained triphenylamine compounds according to the present invention are also shown in Table 3. FIGS. 7 through 10 show the infrared spectra of the thus obtained triphenylamine compounds.

TABLE 3
| Synthesis Example NO. | Aldehyde Compounds | Obtained Products Formula | Melting Point (°C.) | Elemental Analysis Found (Calculated) (%)C | (%)H | (%)N |
|---|---|---|---|---|---|---|
| 6 | 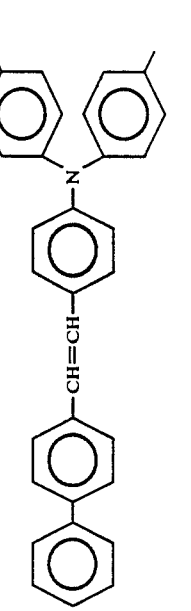 | 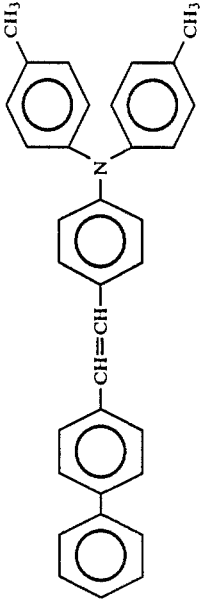 | 208.0–209.5 | 90.27 (90.43) | 6.26 (6.47) | 2.89 (3.10) |
| 7 | 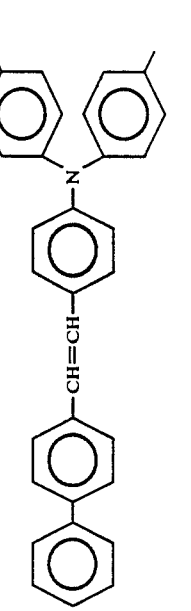 | 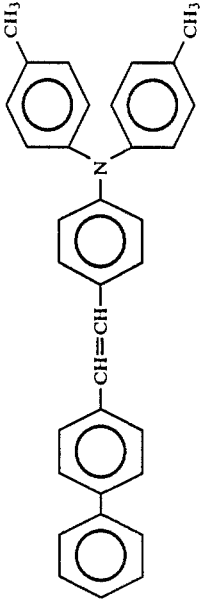 | 222.5–224.0 | 90.90 (90.73) | 5.72 (5.96) | 3.29 (3.31) |
| 8 | 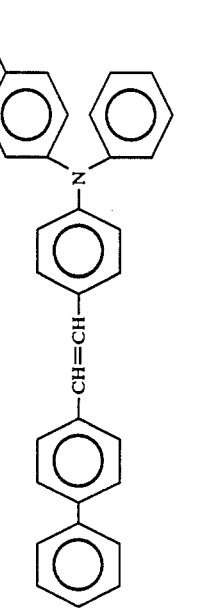 | 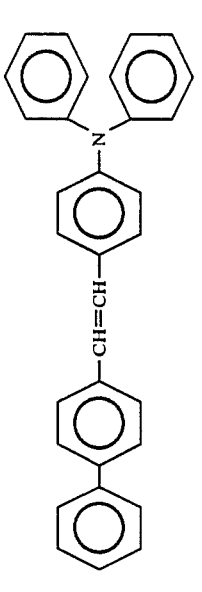 | 195.5–196.0 | 84.62 (88.44) | 5.97 (6.04) | 2.62 (2.90) |
| 9 | 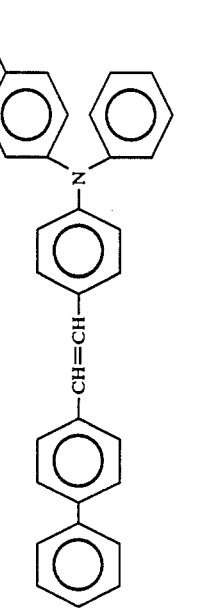 | 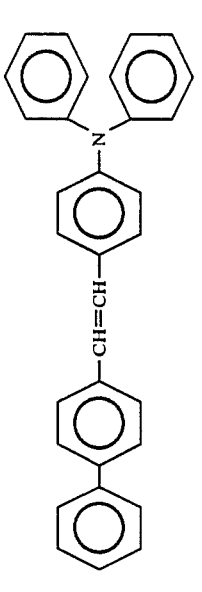 | 183.0–183.7 | 87.56 (87.38) | 5.86 (6.00) | 2.82 (3.09) |

TABLE 3-continued
| Synthesis Example NO. | Aldehyde Compounds | Obtained Products Formula | Melting Point (°C.) | Elemental Analysis Found (Calculated) | | |
|---|---|---|---|---|---|---|
| | | | | (%)C | (%)H | (%)N |
| 10 |  |  | 189.0–190.0 | 90.81 (90.58) | 6.00 (6.22) | 2.94 (3.20) |

EXAMPLE 1

76 parts by weight of Diane Blue (C.I. Pigment Blue 25, CI21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

2 parts by weight of 1-[4-N,N-bis(p-tolyl)aminophenyl]-2-(4-biphenyl)ethane (triphenylamine compound No. 2 in Table 1) prepared in the above-mentioned Synthesis Example 1, 2 parts by weight of polycarbonate resin (Trademark "Panlite K-1300" made by Teijin Limited.) and 16 parts by weight of tetrahydrofuran were mixed to form a solution. This solution was coated on the above formed charge generation layer by a doctor blade and then dried at 80° C. for 2 minutes and then at 120° C. for 5 minutes, so that a charge transport layer having a thickness of about 20 μm was formed on the charge generation layer. Thus a two-layered type electrophotographic photoconductor No. 3 according to the present invention was prepared.

EXAMPLES 2 TO 28

The procedure for Example 1 was repeated except that Diane Blue serving as a charge generating material and the triphenylamine compound No. 2 serving as a charge transporting material employed in Example 1 were replaced by the respective charge generating materials and charge transporting materials shown in the following Table 4, whereby two-layered type electrophotographic photoconductors No. 2 to No. 28 according to the present invention were prepared.

TABLE 4
| Photoconductor No. | Charge Generating Material | Charge Transporting Material (Triphenylamine Compound No.) |
|---|---|---|
| 1 | 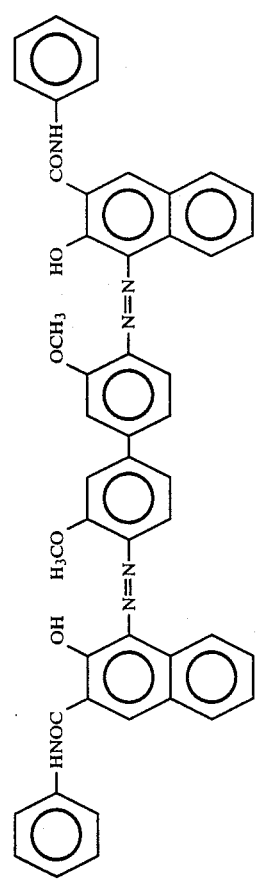 | 2 |
| 2 | 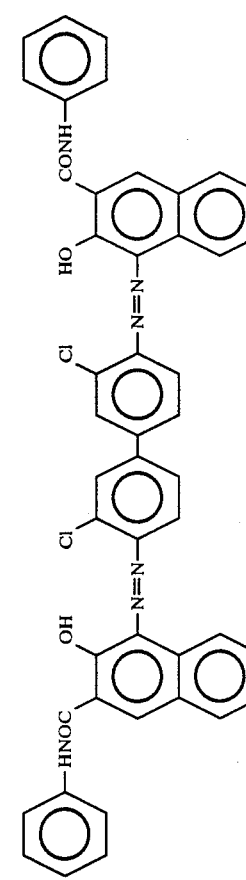 | 2 |
| 3 | 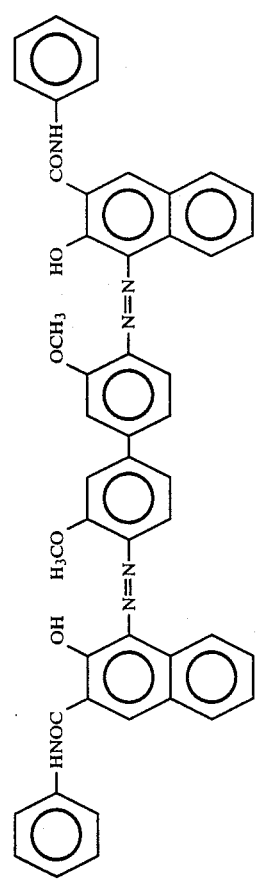 (hereinafter referred to as CG-1) | 2 |

TABLE 4-continued

| Photoconductor No. | Charge Generating Material | Charge Transporting Material (Triphenylamine) Compound No. |
|---|---|---|
| 4 | (structure) | 2 |
| 5 | (structure) (hereinafter referred to as CG-2) | 2 |

TABLE 4-continued

| Photoconductor No. | Charge Generating Material | Charge Transporting Material (Triphenylamine Compound No.) |
|---|---|---|
| 6 | (structure shown) | 2 |
| 7 | β-type copper phthalocyanine | 2 |
| 8 | (structure shown) | 16 |

TABLE 4-continued

| Photoconductor No. | Charge Generating Material | Charge Transporting Material (Triphenylamine Compound No.) |
|---|---|---|
| 9 | (structure shown) | 16 |
| 10 | CG-1 | 1 |
| 11 | CG-1 | 5 |
| 12 | CG-1 | 8 |
| 13 | CG-2 | 9 |
| 14 | CG-1 | 12 |
| 15 | CG-1 | 16 |
| 16 | CG-1 | 19 |
| 17 | CG-1 | 30 |
| 18 | CG-1 | 33 |
| 19 | CG-2 | 1 |
| 20 | CG-2 | 5 |
| 21 | CG-2 | 8 |
| 22 | CG-2 | 9 |
| 23 | CG-2 | 12 |
| 24 | CG-2 | 16 |
| 25 | CG-2 | 19 |
| 26 | CG-2 | 30 |
| 27 | CG-2 | 33 |
| 28 | CG-2 | 40 |

EXAMPLE 29

Selenium was vacuum-deposited on an aluminum plate having a thickness of about 300 μm, so that a charge generation layer having a thickness of about 1 μm was formed on the aluminum plate.

2 parts by weight of 1-[4-N,N-bis(p-tolyl)aminophenyl]-2-(4-biphenyl)ethane (triphenylamine compound No. 2) prepared in the above-mentioned Synthesis Example 1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by a doctor blade, dried at room temperature, and then dried under reduced pressure, so that a charge transport layer having a thickness of about 10 μm was formed on the charge generation layer. Thus a two-layered type electrophotographic photoconductor No. 29 according to the present invention was prepared.

EXAMPLE 30

A perylene pigment having the following formula was vacuum-deposited on an aluminum plate having a thickness of about 300 μm, so that a charge generation layer having a thickness of about 0.6 μm was formed on the aluminum plate:

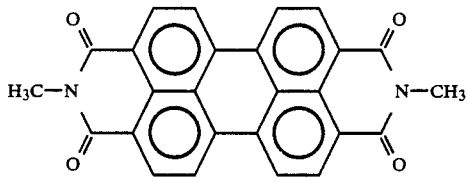

2 parts by weight of the triphenylamine compound No. 16 in Table 1, 3 parts by weight of polyester resin (Trademark "Polyester Adhesive 49000" made by Du Pont de Nemours, E.I. & Co.) and 45 parts by weight of tetrahydrofuran were mixed to form a solution. This solution was coated on the above formed charge generation layer by doctor blade, dried at room temperature, and then dried under reduced pressure, so that a charge transport layer having a thickness of about 10 μm was formed on the charge generation layer. Thus a two-layered type electrophotographic photoconductor No. 30 according to the present invention was prepared.

EXAMPLE 31

A mixture of 1 part by weight of the same Diane Blue as employed in Example 1 and 158 parts by weight of tetrahydrofuran was dispersed and ground in a ball mill to form a dispersion. To the thus formed dispersion, 12 parts by weight of triphenylamine compound No. 2 in Table 1 and 18 parts by weight of polyester resin (Trademark "Polyester Adhesive 49000" made by Du Pont de Nemours, E.I. & Co.) were added to form a solution. This solution was coated on an aluminum surface of an aluminum-deposited polyester film by a doctor blade, and dried at 100° C. for 30 minutes, so that a photoconductive layer having a thickness of about 16 μm was formed on the aluminum-deposited polyester film. Thus, an electrophotographic photoconductor No. 31 was prepared.

EXAMPLE 32

The procedure for Example 5 was repeated except that 1-[4-N,N-bis(p-tolyl)aminophenyl]-2-(4-biphenyl)ethane (triphenylamine compound No. 2 in Table 1) employed in Example 5 as a charge transporting material was replaced by the triphenylamine compound prepared in Synthesis Example 8, whereby a two-layered type electrophotographic photoconductor No. 32 according to the present invention was prepared.

Each of the thus prepared electrophotographic photoconductors No. 1 through No. 32 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Each electrophotographic photoconductor was then allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 4.5 lux, and the exposure $E_{\frac{1}{2}}$ (lux·sec) required to reduce the initial surface potential Vpo (V) to ½ the initial surface potential Vpo (V) was measured. The results are shown in Table 5.

TABLE 5

| Photoconductor No. | Vpo (V) | $E_{\frac{1}{2}}$ (lux · sec) |
| --- | --- | --- |
| 1 | −1300 | 2.80 |
| 2 | −1100 | 2.10 |
| 3 | −1221 | 1.02 |
| 4 | −1250 | 3.30 |
| 5 | −1221 | 1.07 |
| 6 | −1100 | 1.15 |
| 7 | −1020 | 2.25 |
| 8 | −1250 | 2.60 |
| 9 | −1050 | 2.05 |
| 10 | −1408 | 1.11 |
| 11 | −1340 | 1.10 |
| 12 | −1418 | 1.21 |
| 13 | −1423 | 1.15 |
| 14 | −1300 | 1.05 |
| 15 | −1200 | 1.00 |
| 16 | −1250 | 1.05 |
| 17 | −1180 | 1.02 |
| 18 | −1050 | 1.00 |
| 19 | −1290 | 1.54 |
| 20 | −864 | 0.99 |
| 21 | −1197 | 1.32 |
| 22 | −1244 | 1.29 |
| 23 | −1050 | 1.02 |
| 24 | −1200 | 1.05 |
| 25 | −870 | 0.93 |
| 26 | −1090 | 1.08 |
| 27 | −830 | 0.92 |
| 28 | −1280 | 1.12 |
| 29 | −1050 | 2.20 |
| 30 | −1100 | 4.20 |
| 31 | +1200 | 2.60 |
| 32 | −596 | 1.58 |

Each of the above-mentioned electrophotographic photoconductors according to the present invention was incorporated in a commercially available electrophotographic copying machine and charged negatively or positively. Then it was exposed to the light through an original to form a latent electrostatic image on the surface of the photoconductor. The thus formed latent electrostatic image was developed by a dry-type developer to a visible image. The thus obtained visible image was transferred to a sheet of plain paper and fixed thereon, so that a clear image was formed. In the case where a wet-type developer was employed, a clear image was formed likewise.

The electrophotographic photoconductor according to the present invention comprises a photoconductive layer comprising specific triphenylamine compounds serving as an organic photoconductive material. As a result, the resistance to heat and mechanical shocks of the photoconductor can be improved as well as the photoconductive properties thereof, and further the photoconductor according to the present invention can be manufactured at relatively low cost.

What is claimed is:

1. An electrophotographic photoconductor comprising an electroconductive support and a photoconductive layer formed thereon comprising as an effective component at least one triphenylamine compound represented by formula (I):

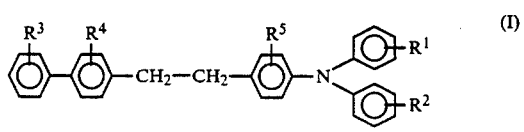

wherein $R^1$, $R^2$, $R^3$, $R^4$ and $R^5$ each represent hydrogen, an alkyl group having 1 to 4 carbon atoms, an alkoxyl group having 1 to 4 carbon atoms, or a halogen, which may be the same or different.

2. The electrophotographic photoconductor as claimed in claim 1, wherein $R^3$, $R^4$ and $R^5$ in formula (I) each represent hydrogen.

3. The electrophotographic photoconductor as claimed in claim 1, wherein said photoconductive layer comprises a charge generating material and a charge transporting medium comprising said triphenylamine compound and a binder agent, in which said charge generating material is dispersed.

4. The electrophotographic photoconductor as claimed in claim 1, wherein said photoconductive layer comprises a charge generation layer containing a charge generating material, and a charge transport layer containing said triphenylamine compound as a charge transporting material.

5. The electrophotographic photoconductor as claimed in claim 1, wherein the amount of said triphenylamine compound is in the range of 30 wt. % to 70 wt. % of the entire weight of said photoconductive layer.

6. The electrophotographic photoconductor as claimed in claim 3, wherein the amount of said triphenylamine compound is in the range of 10 wt. % to 95 wt. % of the entire weight of said photoconductive layer, and the amount of said charge generating material is in the range of 0.1 wt. % to 50 wt. % of the entire weight of said photoconductive layer.

7. The electrophotographic photoconductor as claimed in claim 4, wherein the amount of said charge generating material is in the range of 10 wt. % to 95 wt. % of the entire weight of said charge generation layer, and the amount of said triphenylamine compound is in the range of 10 wt. % to 95 wt. % of the entire weight of said charge transport layer.

8. A charge transporting material comprising a triphenylamine compound having formula (I):

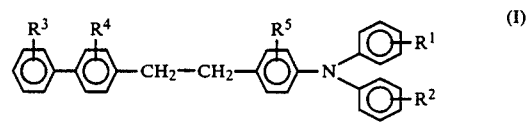

wherein $R^1$, $R^2$, $R^3$, $R^4$ and $R^5$ each represent hydrogen, an alkyl group having 1 to 4 carbon atoms, an alkoxyl group having 1 to 4 carbon atoms, or a halogen, which may be the same or different.

9. The charge transporting material as claimed in claim 8, wherein $R^3$, $R^4$ and $R^5$ in formula (I) each represent hydrogen.

10. An electrophotographic photoconductor comprising an electroconductive support and a photoconductive layer formed thereon comprising as an effective component at least one triphenylamine compound represented by formula (II):

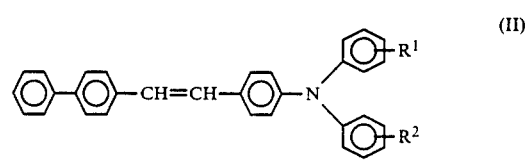

wherein $R^1$ and $R^2$ each represent hydrogen, an alkyl group having 1 to 4 carbon atoms, an alkoxyl group having 1 to 4 carbon atoms, or a halogen, which may be the same or different.

11. The electrophotographic photoconductor as claimed in claim 10, wherein said photoconductive layer comprises a charge generating material and a charge transporting medium comprising said triphenylamine compound and a binder agent, in which said charge generating material is dispersed.

12. The electrophotographic photoconductor as claimed in claim 10, wherein said photoconductive layer comprises a charge generation layer containing a charge generating material, and a charge transport layer containing said triphenylamine compound as a charge transporting material.

13. The electrophotographic photoconductor as claimed in claim 10, wherein the amount of said triphenylamine compound is in the range of 30 wt. % to 70 wt. % of the entire weight of said photoconductive layer.

14. The electrophotographic photoconductor as claimed in claim 11, wherein the amount of said triphenylamine compound is in the range of 10 wt. % to 95 wt. % of the entire weight of said photoconductive layer, and the amount of said charge generating material is in the range of 0.1 wt. % to 50 wt. % of the entire weight of said photoconductive layer.

15. The electrophotographic photoconductor as claimed in claim 12, wherein the amount of said charge generating material is in the range of 10 wt. % to 95 wt. % of the entire weight of said charge generation layer, and the amount of said triphenylamine compound is in the range of 10 wt. % to 95 wt. % of the entire weight of said charge transport layer.

16. A charge transporting material comprising a triphenylamine compound having formula (II):

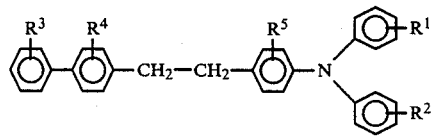

wherein $R^1$ and $R^2$ each represent hydrogen, an alkyl group having 1 to 4 carbon atoms, an alkoxyl group having 1 to 4 carbon atoms, or a halogen, which may be the same or different.

17. A triphenylamine compound having formula (II):

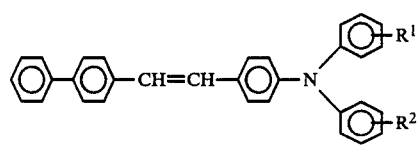

wherein $R^1$ and $R^2$ each represent hydrogen, an alkyl group having 1 to 4 carbon atoms, an alkoxyl group having 1 to 4 carbon atoms, or a halogen, which may be the same or different.

18. The triphenylamine compound as claimed in claim 17, wherein said triphenylamine compound is selected from the group consisting of:

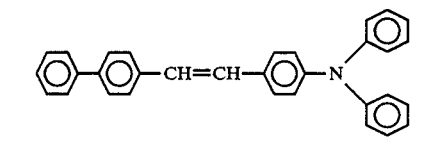

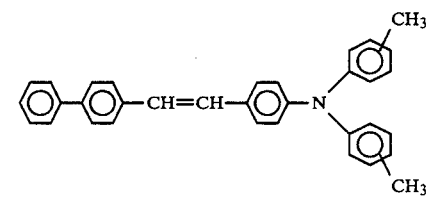

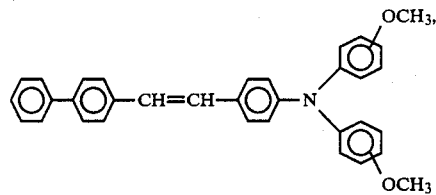

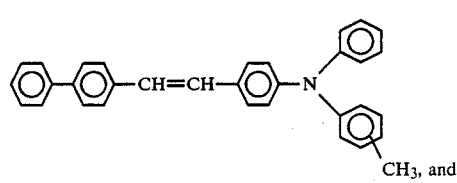

-continued

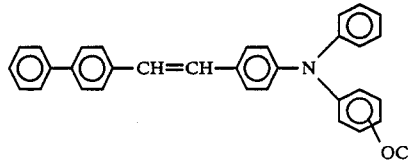

19. A triphenylamine compound having formula (III)

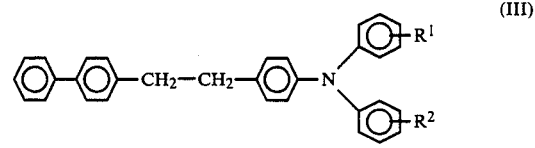

wherein $R^1$ and $R^2$ each represent hydrogen, an alkyl group having 1 to 4 carbon atoms, an akloxyl group having 1 to 4 carbon atoms, or a halogen, which may be the same or different.

20. The triphenylamine compound as claimed in claim 19, wherein said triphenylamine compound is selected from the group consisting of:

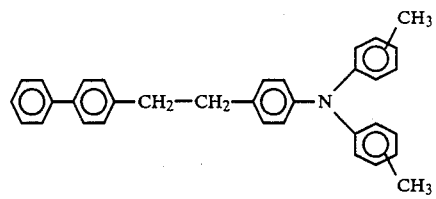

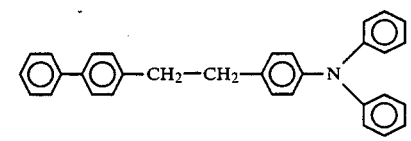

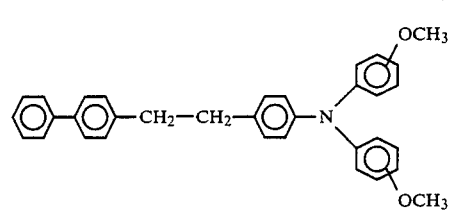

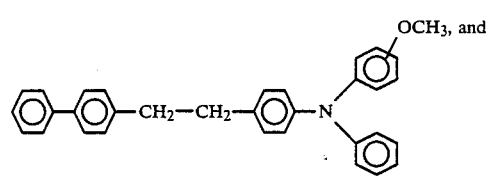

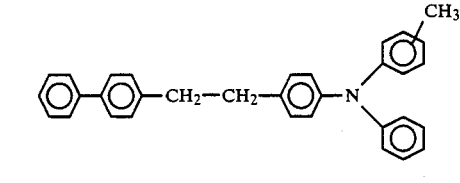

* * * * *

UNITED STATES PATENT AND TRADEMARK OFFICE
CERTIFICATE OF CORRECTION

PATENT NO. : 4,957,838

DATED : September 18, 1990

INVENTOR(S) : Aruga et al.

It is certified that error appears in the above-identified patent and that said Letters Patent is hereby corrected as shown below:

Column 1, line 11, insert a comma --,-- after "photoconductor"

line 63, "are" should read --is--

Column 2, line 14, after "and" insert --are-- line 38, delete "-"

Column 4, line 33, Table 1, after "3-$CH_3$" insert --3-$CH_3$-- in column R4, Compound 39 line 33, Table 1, Compound 39, column R5, insert -- " -- line 68, delete ":" and insert --.--

Column 9, line 61, after "agent" insert --,-- and after "necessary" insert --,--

Column 11 line 16, after "(p-tolyl" insert --)-- line 17, delete ")"

UNITED STATES PATENT AND TRADEMARK OFFICE
CERTIFICATE OF CORRECTION

PATENT NO. : 4,957,838

DATED : September 18, 1990

INVENTOR(S) : Aruga, et al.

It is certified that error appears in the above-identified patent and that said Letters Patent is hereby corrected as shown below:

Column 11, line 41, after "(p-tolyl" insert --)-- line 42, delete ")"

Column 12, line 33, "styrylibipheyl" should read --styrylibiphenyl--

Column 17, line 21, "wa" should read --was--

Signed and Sealed this

Fourteenth Day of July, 1992

*Attest:*

DOUGLAS B. COMER

*Attesting Officer*      *Acting Commissioner of Patents and Trademarks*